United States Patent [19]

Durham et al.

[11] Patent Number: 5,032,125
[45] Date of Patent: Jul. 16, 1991

[54] INTRAMEDULLARY HIP SCREW

[75] Inventors: A. Glenn Durham, Memphis, Tenn.; David L. Brumfield, Nesbit, Miss.

[73] Assignee: Smith & Nephew Richards Inc., Memphis, Tenn.

[21] Appl. No.: 476,188

[22] Filed: Feb. 6, 1990

[51] Int. Cl.⁵ ............................................. A61F 5/04
[52] U.S. Cl. ..................................... 606/62; 606/65; 606/72; 606/73
[58] Field of Search ........................... 606/62–68, 606/70, 81, 89; 623/16, 17, 23

[56] References Cited

U.S. PATENT DOCUMENTS

| | | | |
|---|---|---|---|
| 3,433,220 | 3/1969 | Zickel | 606/64 |
| 4,438,762 | 3/1984 | Kyle | 606/65 |
| 4,621,629 | 11/1986 | Koeneman | 606/65 |
| 4,622,959 | 11/1986 | Marcus | 606/64 |
| 4,657,001 | 4/1987 | Fixel | 606/66 |
| 4,667,664 | 5/1987 | Taylor | 606/64 |
| 4,697,585 | 10/1987 | Williams | 606/64 |
| 4,733,654 | 3/1988 | Marino | 606/64 |
| 4,776,330 | 10/1988 | Chapman | 606/64 |
| 4,805,607 | 2/1989 | Engelhardt | 606/64 |
| 4,827,917 | 5/1989 | Brumfield | 606/64 |

FOREIGN PATENT DOCUMENTS

| | | | |
|---|---|---|---|
| 0321170 | 6/1989 | European Pat. Off. | 606/62 |
| 2209947 | 6/1989 | United Kingdom | 606/65 |

*Primary Examiner*—Robert A. Hafer
*Assistant Examiner*—Michael Brown
*Attorney, Agent, or Firm*—Kirkpatrick & Lockhart

[57] ABSTRACT

An intramedullary hip screw is provided which includes an intramedullary rod, a lag screw and a sleeve for slidably receiving the lag screw. The sleeve is received in a passage in the intramedullary rod having an axis positioned at an angle relative to the longitudinal axis of the intramedullary rod such that the axis of the sleeve is directed toward the head of the femur. The intramedullary hip screw of the present invention permits sliding compression of selected fractures, particularly intertrochanteric fractures and fractures of the femoral neck.

4 Claims, 2 Drawing Sheets

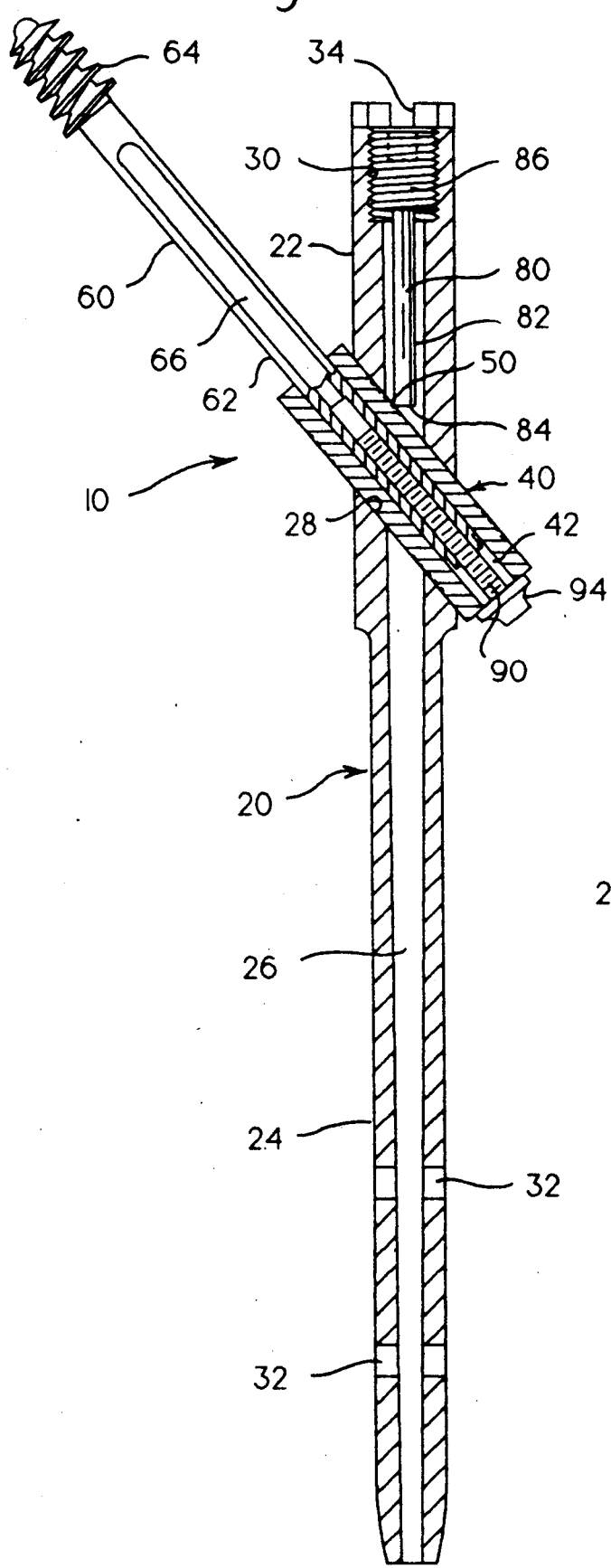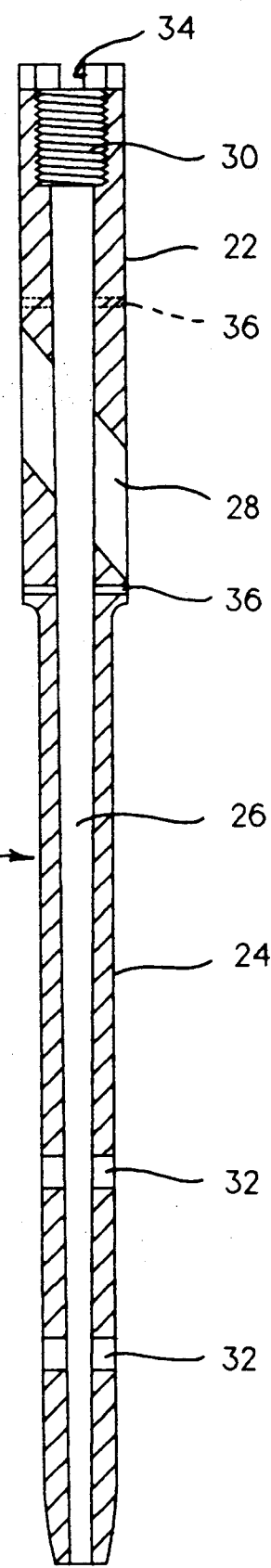

INTRAMEDULLARY HIP SCREW

BACKGROUND OF THE INVENTION

1. Field of the Invention

The present invention relates to devices for treating femoral fractures.

2. Description of the Prior Art

There are a variety of devices used to treat femoral fractures. Fractures of the neck or head, as well as intertrochanteric fractures of the femur have been successfully treated with a variety of compression hip screw assemblies which include generally a compression plate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The compressing screw connects the lag screw to the plate. By adjusting the tension of the compressing screw the compression (reduction) of the fracture can be adjusted. The smooth portion of the lag screw must be free to slide through the barrel member to permit the adjustment of the compression screw. Because the barrel member is long in comparison to its diameter, the force required to slide and, therefore, maintain reduction of the fracture is minimal. However, compression hip screw assemblies require a long incision in the tissue around the fracture and the compression plate, positioned on the outside of the bone, is displaced from the application of force thereby creating a long moment arm and subjecting the implant to very high tensile forces.

Compression hip screw assemblies are shown by the following patents: Fixel, U.S. Pat. No. 4,432,358; Calender, Jr., U.S. Pat. No. 3,374,786; Pugh et al., U.S. Pat. No. 2,702,543; Griggs, U.S. Pat. No. 4,530,355; Blosser, U.S. Pat. No. 3,094,120; and Wagner, U.S. Pat. No. 3,842,825. The Blosser and Wagner patents illustrate the use of multiple screws to prevent rotation of the lag screw relative to the compression plate and barrel member. A surgical bone pin which functions like a lag screw and compressing screw but which does not include a compression plate is shown by Cochran et al., U.S. Pat. No. 3,103,926.

Subtrochanteric and femoral shaft fractures have been treated with the help of intramedullary rods which are inserted into the intramedullary canal of the femur to immobilize the femoral parts involved in fractures. A single angled cross-nail or locking screw is inserted through the femur and the proximal end of the intramedullary rod. In some varieties, one or two screws may also be inserted through the femoral shaft and through the distal end of the intramedullary rod. The standard intramedullary rods have been successfully employed in treating fractures in lower portions of the femoral shaft.

The Grosse-Kempf nail manufactured by Howmedica Company of Rutherford, New Jersey is believed to be one of the earliest intramedullary nailing devices introduced into the United States. The Grosse-Kempf nail includes a threaded hole in the intramedullary rod for receiving the interlocking screw. The fully threaded screw cannot slide through the threaded hole to permit the type of compression found in the compression hip screw assemblies discussed above. Furthermore, the axis of the threaded hole coincides with a line between the greater to lesser trochanter and not in the direction of the femoral neck.

Zickel, U.S. Pat. No. 3,433,220, which issued on Mar. 18, 1969, discloses an intramedullary rod and cross-nail assembly which is useful in treating fractures occurring in the upper one-third or subtrochanteric portion of the femur. The Zickel nail is a solid intramedullary nail having a single proximal tri-flange cross-nail which is inserted in the direction of the femoral head.

The rigid tri-flange cross-nail is not suitable for use in treating femoral neck fractures because the cross-nail must be locked into position by a set screw to prevent backing out. Adequate compression cannot be achieved. As stated above, the sliding compression screw has been found to be most effective in treating femoral neck fractures.

A femoral fracture device which includes an intramedullary rod and a screw inserted through the proximal portion of the rod in the direction of the femoral head which is designed to permit sliding compression of selected fractures is described in Brumfield, U.S. Pat. No. 4,827,917. The device of the Brumfield patent combines the superior mechanical and biological attributes of intramedullary fixation with the proven benefits of the sliding compression screw.

An object of the present invention is to improve upon the benefits achieved by the Brumfield patent by more closely providing the slidability and consequent reduction of the fracture heretofore available only with conventional compression hip screw assemblies.

SUMMARY OF THE INVENTION

The present invention provides an apparatus for treating fractures of the femur which includes a lag screw, a sleeve and an intramedullary rod. The lag screw has an elongate body member and engaging means formed at one end thereof adapted in use to engage the head of a femur. The intramedullary rod has a longitudinal axis, a proximal head and a stem distal thereto. The rod is adapted in use for insertion into the intramedullary canal of the femur. The head of the rod has at least one passage extending therethrough for receiving the sleeve. The hollow sleeve slidably receives the lag screw. The passage in the rod is positioned in an angled direction relative to the longitudinal axis of the rod such that when the rod is in position in the intramedullary canal of the femur, the axis of the passage, and the sleeve and the lag screw when inserted through the passage, are directed toward the head of the femur.

Means, such as a compression screw receivable in the lag screw, are preferably provided for cooperation with the lag screw and the sleeve to apply a sliding compressive force to selected fractures of the femur. The sleeve may include an engaging surface formed on the interior of the sleeve and adapted for cooperation with a complementary engaging surface formed on the body member of the lag screw to prevent rotation of the lag screw within the sleeve.

BRIEF DESCRIPTION OF THE DRAWINGS

The intramedullary hip screw of the present invention can be better understood by reference to the drawings in which:

FIG. 1 is a side elevation section view of the preferred embodiment of the intramedullary hip screw of the present invention;

FIG. 2 is a side elevation section view of the intramedullary rod of FIG. 1;

DETAILED DESCRIPTION OF THE PREFERRED EMBODIMENTS

Figure 3:
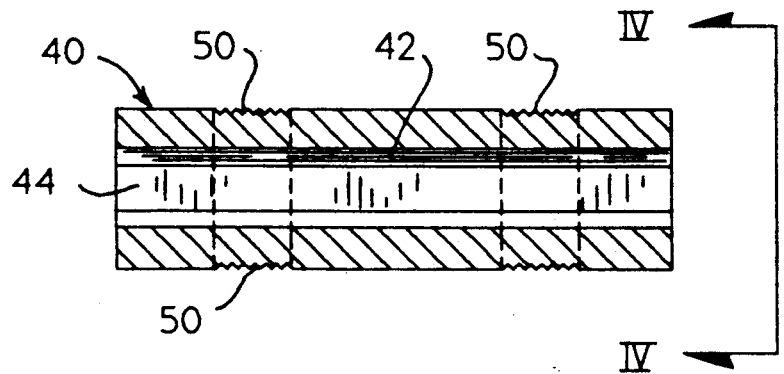
FIG. 3 is a side elevation section view of the sleeve of FIG. 1.

FIGS. 1-6 illustrate the preferred embodiment of the components of intramedullary hip screw 10 of the present invention. The intramedullary hip screw 10 includes generally an intramedullary rod 20, a sleeve 40 and a lag screw 60. A set screw 80 and a compression screw 90 are also provided in the preferred embodiment of the invention. The intramedullary hip screw 10 may be made of any suitable strong, biocompatible material. Stainless steel, titanium or chrome-cobalt are preferred.

Referring to FIG. 2, the intramedullary rod 20 includes a proximal head 22, a stem 24 distal to the head 22 and an optional longitudinal bore 26. Head 22 includes a passage 28 which extends through rod 20. The axis of passage 28 is angled relative to the longitudinal axis of the rod 20 and in use, is directed toward the femoral head. The angle is preferably between about 30°-50°. The bore 26 preferably extends through the entire length of rod 20 but may extend only partially along the length of rod 20.

Rod 20 also includes an internally threaded counter bore 30 with slots 34 at the opening for receiving threaded set screw 80 and the prongs of a tool for aligning rod 20 within the femur. In one embodiment of rod 20, holes 32 (two are shown) are provided through which bolts, screws, nails or some other suitable known anchoring means may be passed to anchor the stem 24 of rod 20 in place within the intramedullary canal of the femur. Holes 32 extend through bore 26 in a transverse, preferably perpendicular, direction relative to the longitudinal axis of rod 20. There may be a plurality of holes 32 or more desired locations. In another embodiment of rod 20, there may be no holes 32.

Augmentation holes 36 may be provided in head 22 of rod 20 through which additional anchoring pins (not shown) may be passed to provide additional fixation. The augmentation holes 36, if provided, are smaller than passage 28. If positioned above passage 28 they must be off center to permit the pins to clear set screw 80.

Figure 4:
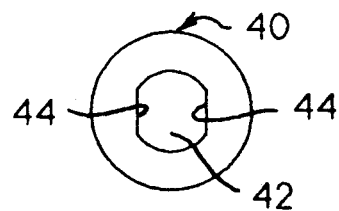
FIG. 4 is a section view through the line IV—IV of FIG. 3.
Figure 5:
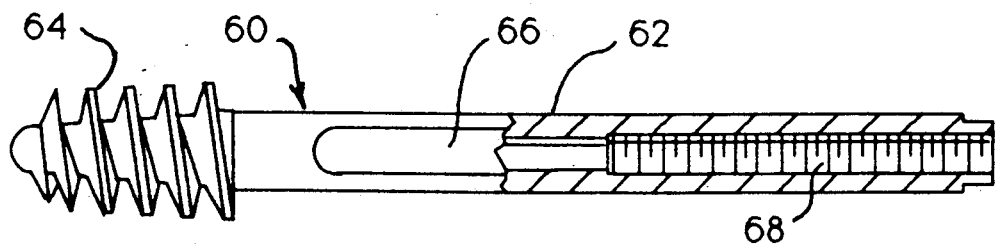
FIG. 5 is a side elevation section view of the lag screw of FIG. 1.
Figure 6:
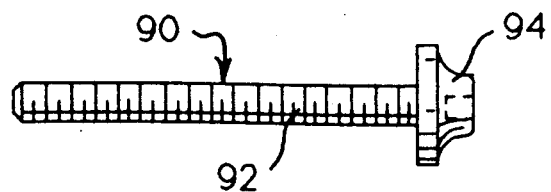
FIG. 6 is a side elevation view of the compression screw of FIG. 1.

Sleeve 40, as shown in FIGS. 1 and 3, includes a central bore 42. Sleeve 40 is received in passage 28 of rod 20 and is longer than passage 28. The length of sleeve 40 is greater than its diameter in the relative proportions typical of the barrel members of compression plates as used in prior art devices. Bore 42 is preferably keyed. Referring to FIG. 4, the bore 42 includes opposing flat surfaces 44. The exterior surface of sleeve 40 preferably, includes grooves 50 for cooperation with set screw 80.

Lag screw 60 includes elongate body member 62 and threaded end 64. Body member 62 is preferably also keyed and, to that end, includes opposing flat surfaces 66 which complement and cooperate with the flat surfaces 44 of sleeve 40. As shown in FIG. 1, lag screw 60 is slidably received within sleeve 40. The surfaces 44 and 66 cooperate to prevent lag screw 60 from rotating within sleeve 40 while permitting lag screw 60 to slide axially within sleeve 40. The external diameter of the threads on threaded end 64 is preferably greater than the diameter of body member 62. The outside diameter of sleeve 40 is preferably approximately equal to the outside diameter of the threads on lag screw 60. The dimensions of threaded end 64 permit greater purchase of the femoral head which is particularly advantageous in treating the elderly or those with degenerative bone disorders.

Lag screw 60 also includes at its trailing end, an engaging portion in the form of an internally threaded bore 68 for receiving threaded compression screw 90. Compression screw 90 cooperates with lag screw 60 and sleeve 40 to apply compressive sliding forces to the fracture.

Compression screw 90 includes a first portion, e.g. a threaded shank 92 and a second portion, e.g. a flat-bottomed head 94, the diameter of which is greater than the diameter of bore 42 of sleeve 40. Thus, when compression screw 90 is tightened within lag screw 60, head 94 presses against the end of sleeve 40 to provide the compression heretofore found only in a compression hip screw assembly having a compression plate external to the bone. Thus, compression screw 90 provides a means for cooperation with the lag screw and the sleeve for applying sliding compressive forces to selected fractures of the femur.

The set screw 80 preferably has a smooth shank 82, a flat bottom portion 84 and a threaded head portion 86. The flat bottom portion 84 is a preferred means of engaging groove 50 of sleeve 40, when present, to provide superior mechanical interlocking of the components. Threads on head portion 86 engage the threads in counter bore 30 of rod 20.

Alternative embodiments of the intramedullary hip screw 10 of the present invention may include a rod 20 of varying lengths. The rod 20 may have an internal bore as shown, a partial bore or may be solid in cross section except for passage 28 and any holes 32 or 36.

The intramedullary hip screw 10 of the present invention may be inserted into a patient by any suitable known technique. Generally, the intramedullary canal of the femur is first reamed with an appropriate known tool to create a void for insertion of rod 20. The void is preferably over reamed by about one millimeter to permit sufficient space for blood flow after insertion of the rod 20. A guide pin or wire is optionally inserted into the reamed intramedullary canal of the femur. Then rod 20 is introduced into the desired position. When rod 20 includes bore 26, rod 20 is introduced over the guide wire. The position should be confirmed by image intensification.

When rod 20 is properly oriented, the lag screw 60 is aligned with passage 28 by a suitable known tool. The site is appropriately reamed and lag screw 60 is inserted through passage 28 with the aid of a guide wire and suitable known tools. The threaded end 64 of lag screw 60 engages the femoral head. The smooth elongate body member 62 slides easily within passage 28.

Sleeve 40 is inserted over the body member 62 of lag screw 60 into passage 28 of rod 20. Surfaces 44 of sleeve 40 align with surfaces 66 of body member 62. Set screw 80 is then inserted through the top of rod 20 and tightened until an edge of bottom portion 84 engages a groove 50 on sleeve 40 to secure sleeve 40 within passage 28.

Compression screw 90 is then optionally inserted into bore 68 of lag screw 60 and tightened with a suitable tool until the flat bottom portion of head 94 presses against the end of sleeve 40. The compression screw 90 is tightened to cooperate with lag screw 60 and sleeve 40 to apply the desired compressive force to the fracture. The smooth elongate body member 62 of lag screw 60 is free to slide within bore 42 of sleeve 40.

If desired, holes are reamed with appropriate tools to create a passage through the bone for insertion of anchoring means through holes 32 in stem 24 of rod 20. Similarly, if desired, appropriately sized holes are reamed to permit the insertion of anchoring pins in augmentation holes 36 of head 22 of rod 20.

The intramedullary hip screw 10 of the present invention provides an advantage over conventional compression screw assemblies because it requires a much smaller incision for insertion, thereby reducing added trauma to the fracture area. Passing the lag screw 60 and sleeve 40 through an intramedullary rod reduces the applied moment arm significantly and therefore, decreases the loads that the implant must carry. Decreasing the load on the implant reduces the chance of implant failure. The design of intramedullary hip screw 10 offers enhanced fracture compression in comparison to femoral fracture devices heretofore available by providing a greater area of slidability for lag screw 60. The length of sleeve 40 through which body member 62 of lag screw 60 slides is greater than the comparable area of slidability provided, for example, in the femoral fracture device of Brumfield, U.S. Pat. No. 4,827,917 discussed previously herein. Compression screw 90, in cooperation with sleeve 40 and lag screw 60 provide the same benefits of sliding compression available in compression hip screw assemblies and the same fixation benefits of intramedullary rods while eliminating the high tensile forces placed on the implant in compression hip screw assemblies.

What is claimed is:

1. Apparatus for treating fractures of the femur comprising:
    a lag screw having a smooth elongate body member and engaging means formed at one end thereof adapted in use to engage the head of a femur;
    a hollow sleeve for slidably receiving said lag screw; and
    an intramedullary rod having a longitudinal axis, said rod having a proximal head, a longitudinal bore extending at least partially therethrough, engaging means formed on the exterior of said sleeve, and a stem distal thereto and being adapted in use for insertion into the intramedullary canal of the femur, said head having at least one passage extending therethrough for receiving said sleeve, said passage being positioned in an angled direction relative to said longitudinal axis of said rod such that when said rod is in position within the intramedullary canal of the femur, the axis of said passage is directed toward the head of the femur.

2. The apparatus recited in claim 1 wherein said body member of said lag screw has a trailing end and an engaging portion formed at said trailing end, and said apparatus further comprises means having a first portion for cooperation with said engaging portion of said lag screw and a second portion for cooperation with said sleeve for applying sliding compressive forces to selected fractures of the femur.

3. The apparatus recited in claim 1 further comprising a first engaging surface formed on the interior surface of said sleeve and a complementary engaging surface formed on the exterior of said body member of said lag screw, said first and complementary engaging surfaces being configured to cooperate to prevent rotation of said lag screw when said lag screw is inserted in said sleeve.

4. The apparatus recited in claim 1 further comprising a set screw for insertion through said bore of said rod to lockingly engage said engaging means on said sleeve.

* * * * *

UNITED STATES PATENT AND TRADEMARK OFFICE
CERTIFICATE OF CORRECTION

PATENT NO. : 5,032,125
DATED : July 16, 1991
INVENTOR(S) : A. Glenn Durham and David L. Brumfield It is certified that error appears in the above-identified patent and that said Letters Patent is hereby corrected as shown below:

```
    Col. 3, line 47, after "32" insert the following
--along the length of stem 24 to permit anchoring in any
one--.
```

Signed and Sealed this

Tenth Day of November, 1992

Attest:

DOUGLAS B. COMER

*Attesting Officer*    Acting Commissioner of Patents and Trademarks